United States Patent
Aslanian et al.

[11] Patent Number: 6,034,251
[45] Date of Patent: Mar. 7, 2000

[54] PHENYL-ALKYL-IMIDAZOLES

[75] Inventors: Robert G. Aslanian, Rockaway; Kevin D. McCormick, Edison; John J. Piwinski, Clinton Township, all of N.J.

[73] Assignee: Schering Corporation, Kenilworth, N.J.

[21] Appl. No.: 09/185,972

[22] Filed: Nov. 5, 1998

Related U.S. Application Data

[60] Provisional application No. 60/064,937, Nov. 7, 1997.

[51] Int. Cl.$^7$ .................... C07D 233/54; C07D 233/60; C07D 233/61; C07D 233/90; A61K 31/415
[52] U.S. Cl. ........................... 548/338.1; 548/341.1; 548/341.5; 548/342.1; 514/399; 514/400
[58] Field of Search ................ 548/338.1, 341.1, 548/341.5, 342.1; 514/399, 400

[56] References Cited

U.S. PATENT DOCUMENTS

| | | | |
|---|---|---|---|
| 4,707,487 | 11/1987 | Arrang et al. | 514/326 |
| 5,376,671 | 12/1994 | Muller-Gliemann et al. | 514/399 |
| 5,521,206 | 5/1996 | Muller et al. | 514/400 |
| 5,534,537 | 7/1996 | Ciccarone et al. | 514/397 |
| 5,559,113 | 9/1996 | Schwartz et al. | 514/252 |
| 5,578,616 | 11/1996 | Aslanian et al. | 514/341 |
| 5,622,982 | 4/1997 | Schuster et al. | 514/399 |
| 5,708,171 | 1/1998 | Schwartz et al. | 544/327 |
| 5,869,479 | 2/1999 | Kreutner et al. | 514/212 |

FOREIGN PATENT DOCUMENTS

| | | |
|---|---|---|
| 0 197 840 A1 | 10/1986 | European Pat. Off. . |
| WO 93 12107 | 6/1993 | WIPO . |
| WO 93 12108 | 6/1993 | WIPO . |
| WO 93 14070 | 7/1993 | WIPO . |
| 94/19326 | 9/1994 | WIPO ................ 548/338.1 |
| WO 95 06037 | 3/1995 | WIPO . |
| WO 95 14007 | 5/1995 | WIPO . |
| WO 96 29315 | 9/1996 | WIPO . |
| WO 98 06394 | 2/1998 | WIPO . |

OTHER PUBLICATIONS

Partial translation for WO 9629315.

*Primary Examiner*—Floyd D. Higel
*Attorney, Agent, or Firm*—Henry C. Jeanette

[57] ABSTRACT

Disclosed are novel phenyl-alkyl-imidazoles of the formula

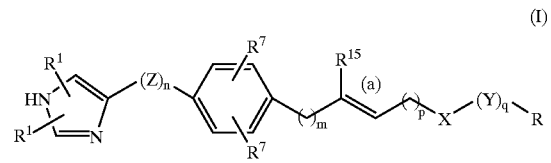

(I)

wherein $R^1$, $R^7$, m, n, p, q, X, Y, Z, R and $R^{15}$ are as defined in the specification.

Also disclosed are pharmaceutical compositions comprising the compounds of formula I.

Further disclosed are methods of treating allergy, inflammation, hypotension, glaucoma, sleeping disorders, states of hyper and hypo motility of the gastrointestinal tract, hypo and hyperactivity of the central nervous system, Alzheimer's, schizophrenia, obesity and migraines by administering compounds of formula I.

Also disclosed are methods for treatment of upper airway allergic responses comprising administering a compound, or salt or solvate thereof, of formula I in combination or admixture with a histamine $H_1$ receptor antagonist.

24 Claims, No Drawings

PHENYL-ALKYL-IMIDAZOLES

REFERENCE TO RELATED APPLICATIONS

This application claims the benefit of U.S. Provisional Application Ser. No. 60/064,937 filed Nov. 7, 1997.

FIELD OF THE INVENTION

The present invention relates to novel phenyl-alkyl-imidazoles having valuable pharmacological properties, especially CNS activities and activity against inflammatory disease. Compounds of this invention are antagonists of the $H_3$ receptor.

BACKGROUND OF THE INVENTION

European Patent Application No. 0 420 396 A2 (Smith Kline & French Laboratories Limited) and Howson et al., *Bioorg. & Med. Chem. Letters*, Vol. 2 No. 1 (1992), pp. 77–78 describe imidazole derivatives having an amidine group as $H_3$ agonists. Van der Groot et al. (*Eur. J. Med. Chem.* (1992) Vol. 27, pp. 511–517) describe isothiourea analogs of histamine as potent agonists or antagonists of the histamine $H_3$ receptor, and these isothiourea analogs of histamine overlap in part with those of the two references cited above. Clapham et al. ["Ability of Histamine $H_3$ Receptor Antagonists to improve Cognition and to increase Acetylcholine Release in vivo in the Rat", British Assn. for Psychopharmacology, Jul. 25–28 1993, reported in *J. Psychopharmacol.* (Abstr. Book), A17] describe the ability of histamine $H_3$ receptor antagonists to improve cognition and to increase release of acetylcholine in vivo in the rat. Clapham et al. ["Ability of the selective Histamine $H_3$ Receptor Antagonist Thioperamide to improve Short-term Memory and Reversal Learning in the Rat", *Brit. J. Pharm. Suppl.*, 1993, 110, Abstract 65P] present results showing that thioperamide can improve short-term memory and reversal learning in the rat and implicate the involvement of $H_3$ receptors in the modulation of cognitive function. Yokoyama et al. ["Effect of thioperamide, a histamine $H_3$ receptor antagonist, on electrically induced convulsions in mice", *Eur. J. Pharmacol.*, vol. 234 (1993), pp. 129–133] report how thioperamide decreased the duration of each phase of convulsion and raised the electroconvulsive threshold, and go on to suggest that these and other findings support the hypothesis that the central histaminergic system is involved in the inhibition of seizures. International Patent Publication No. WO9301812-A1 (SmithKline Beecham PLC) describes the use of S-[3-(4(5)-imidazolyl)propyl] isothiourea as a histamine $H_3$ antagonist, especially for treating cognitive disorders, e.g. Alzheimer's disease and age-related memory impairment. Schlicker et al. ["Novel histamine $H_3$ receptor antagonists: affinities in an $H_3$ receptor binding assay and potencies in two functional $H_3$ receptor models"] describe a number of imidazolylalkyl compounds wherein the imidazolylalkyl group is bonded to a guanidine group, an ester group or an amide group (including thioamide and urea), and compare these to thioperamide. Leurs et al. ["The histamine $H_3$-receptor: A target for developing new drugs", *Progr. Drug Res.* (1992) vol.39, pp.127–165] and Lipp et al. ["Pharmacochemistry of $H_3$-receptors" in *The Histamine Receptor*, eds.: Schwartz and Haas, Wiley-Liss, New York (1992), pp.57–72] review a variety of synthetic $H_3$ receptor antagonists, and Lipp et al. (ibid.) have defined the necessary structural requirements for an $H_3$ receptor antagonist.

WO 95/14007 claims $H_3$ receptor antagonists of the formula

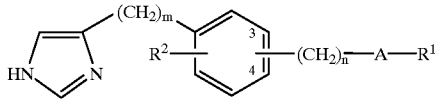

wherein

A is selected from $-O-CO-NR^1-$, $-O-CO-$, $-NR^1-CO-NR^1-$, $-NR^1-CO-$, $-NR^1-$, $-O-$, $-CO-NR^1-$, $-CO-O-$, and $-C(:NR^1)-NR^1-$;

the groups $R^1$, which may be the same or different when there are two or three such groups in the molecule of formula I, are selected from hydrogen, and lower alkyl, aryl, cycloalkyl, heterocyclic and heterocyclylalkyl groups, and groups of the formula $-(CH_2)_y-G$, where G is selected from $CO_2R^3$, $COR^3$, $CONR^3R^4$, $OR^3$, $SR^3$, $NR^3R^4$, heteroaryl and phenyl, which phenyl is optionally substituted by halogen, lower alkoxy or polyhaloloweralkyl, and y is an integer from 1 to 3;

$R^2$ is selected from hydrogen and halogen atoms, and alkyl, alkenyl, alkynyl and trifluoromethyl groups, and groups of the formula $OR^3$, $SR^3$ and $NR^3R^4$;

$R^3$ and $R^4$ are independently selected from hydrogen, and lower alkyl and cycloalkyl groups, or $R^3$ and $R^4$ together with the intervening nitrogen atom can form a saturated ring containing 4 to 6 carbon atoms that can be substituted with one or two lower alkyl groups;

with the proviso that, when y is 1 and G is $OR^3$, $SR^3$ or $NR^3R^4$, then neither $R^3$ nor $R^4$ is hydrogen;

the group $-(CH_2)_n-A-R^1$ is at the 3- or 4-position, and the group $R^2$ is at any free position;

m is an integer from 1 to 3;

and n is 0 or an integer from 1 to 3;

or a pharmaceutically acceptable acid addition salt thereof;

or a pharmaceutically acceptable salt thereof with a base when G is $CO_2H$; including a tautomeric form thereof.

U.S. application Ser. No. 08/689951 filed Aug. 16, 1996 (now abandoned) and U.S. application Ser. No. 08/909319 filed Aug. 14, 1997 (now U.S. Pat. No. 5,869,479 issued Feb. 9, 1999) disclose compositions for the treatment of the symptoms of allergic rhinitis using a combination of at least one histamine $H_1$ receptor antagonist and at least one histamine $H_3$ receptor antagonist.

In view of the art's interest in compounds which affect the $H_3$ receptors, novel compounds having antagonist activity on $H_3$ receptors would be a welcome contribution to the art. This invention provides just such a contribution by providing novel compounds having $H_3$ antagonist activity.

SUMMARY OF THE INVENTION

The present invention provides a compound of the formula I

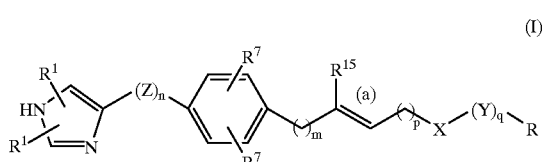

or a pharmaceutically acceptable salt or solvate thereof, wherein:

the double bond (a) is E or Z (that is the double bond to the carbon atom having the $R^{15}$ substituent is of the E or Z configuration);

each $R^1$ is independently selected from the group consisting of hydrogen, lower alkyl, trihalomethyl, phenyl and benzyl;

each $R^7$ is independently selected from the group consisting of hydrogen, lower alkyl, halogen, trihalomethyl, $NR^{10}R^{11}$, or a group $OR^{10}$, whereby $R^{10}$ and $R^{11}$ are independently selected from hydrogen, lower alkyl or trihalomethyl;

X is —$CONR^5$—; —$SO_2$—, —S—; —CO—; —COO—; —$CN(OR^5)NR^5$—; —$C(NR^5)NR^5$—; —$SONR^5$—; —$SO_2NR^5$— and, provided p is not zero, X may also be —O—; —$NR^5$—; —$NR^5CONR^5$—; —$OCONR^5$—; —O—CO— or —$NR^5CO$—;

Y is $C_1$–$C_3$-alkyl, optionally substituted at any carbon atom of the group by one substituent $R^5$;

Z is $C(R^1)_2$; wherein no more than two $R^1$ groups are other than hydrogen;

n is 1 or 2;

m is 0 or 1;

p is 0 or 1;

q is 0 or 1;

R is selected from $C_3$ to $C_7$ cycloalkyl, heterocyclic groups, aryl or heteroaryl, wherein said R groups are optionally substituted with 1–3 substituents as defined below;

each $R^5$ independently represents hydrogen, lower alkyl or poly-haloloweralkyl; and $R^{15}$ represents H or lower alkyl (e.g., methyl).

A further feature of the invention is pharmaceutical compositions containing as active ingredient a compound of the formula I defined above (or a salt, or a solvate, or tautomer) together with a pharmaceutical carrier or excipient.

Further features of the invention are methods for treating inflammation, allergy, diseases of the GI-tract, cardiovascular disease, or disturbances of the central nervous system, which comprise administering to a patient suffering from the corresponding disease (i.e., a patient in need of such treatment) an effective amount of a compound of the formula I defined above (or a salt, solvate or tautomer thereof). For example, a feature of this invention is a method of treating allergy, inflammation, hypotension, glaucoma, sleeping disorders, states of hyper and hypo motility of the gastrointestinal tract, hypo and hyperactivity of the central nervous system, Alzheimer's, schizophrenia, obesity and migraines, comprising administering an effective amount of a compound of formula I (or a salt, solvate or tautomer thereof) to a patient in need of such treatment.

Another feature of this invention is a method for treating inflammation, which comprises administering to a patient suffering from inflammation an effective amount of a compound of formula I (or a salt, solvate or tautomer thereof) to a patient in need of such treatment.

Another feature of this invention is a method for treating allergy, which comprises administering to a patient suffering from allergy an effective amount of a compound of formula I (or a salt, solvate or tautomer thereof) to a patient in need of such treatment.

Another feature of this invention is a method for treating diseases of the GI-tract, which comprises administering to a patient suffering from a disease of the GI-tract an effective amount of a compound of formula I (or a salt, solvate or tautomer thereof) to a patient in need of such treatment.

Another feature of this invention is a method for treating cardiovascular disease, which comprises administering to a patient suffering from cardiovascular disease an effective amount of a compound of formula I (or a salt, solvate or tautomer thereof) to a patient in need of such treatment.

Another feature of this invention is a method for treating disturbances of the central nervous system, which comprises administering to a patient suffering from disturbances of the central nervous system an effective amount of a compound of formula I (or a salt, solvate or tautomer thereof) to a patient in need of such treatment.

The invention also includes the aspect of using the compounds of formula I in combination with a histamine $H_1$ receptor antagonist for treatment of allergy-induced airway (e.g., upper airway) responses.

DETAILED DESCRIPTION OF THE INVENTION

Compounds of the formula I can exist in tautomeric forms by virtue of the imidazole ring: the N-hydrogen atom can tautomerize from one nitrogen atom to the other of that ring. When q is 1 and Y is a substituted alkyl group, or when one $R^1$ substituent of each $(Z)_n$ group is other than H, the compounds of formula I will have asymmetric carbon atoms and will exist in different forms due to such chiral center. All such isomers including diastereomers and enantiomers are covered by the invention.

The compounds of the invention are basic and form pharmaceutically acceptable salts with organic and inorganic acids. Examples of suitable acids for such salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their corresponding salt forms somewhat in certain physical properties, such as solubility in polar solvents, but the salts are otherwise equivalent to their corresponding free base forms for purposes of this invention.

The compounds of Formula I can exist in unsolvated as well as solvated forms, including hydrated forms, e.g., hemi-hydrate. In general, the solvated forms, with pharmaceutically acceptable solvents such as water, ethanol and the like are equivalent to the unsolvated forms for purposes of the invention.

Numerous chemical substances are known to have histamine $H_1$ receptor antagonist activity. Many useful compounds can be classified as ethanolamines, ethylenediamines, alkylamines, phenothiazines or piperidines. Representative $H_1$ receptor antagonists include, without limitation: astemizole, azatadine, azelastine, acrivastine, brompheniramine, cetirizine, chlorpheniramine, clemastine, cyclizine, carebastine, cyproheptadine, carbinoxamine, descarboethoxyloratadine (also known as SCH-34117), diphenhydramine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, picumast, pyrilamine, promethazine, terfenadine, tripelennamine, temelastine, trimeprazine and triprolidine. Other compounds can readily be evaluated to determine activity at $H_1$ receptors by known methods, including specific blockade of the contractile response to histamine of isolated guinea pig ileum. See for example, WO98/06394 published Feb. 19, 1998.

For example, the $H_3$ antagonists of this invention can be combined with an $H_1$ antagonist selected from astemizole, azatadine, azelastine, brompheniramine, cetirizine, chlorpheniramine, clemastine, carebastine, descarboethoxyloratadine (also known as SCH-34117), diphenhydramine, doxylamine, ebastine, fexofenadine, loratadine, levocabastine, mizolastine, norastemizole, or terfenadine.

Also, for example, the $H_3$ antagonists of this invention can be combined with an $H_1$ antagonist selected from, azatadine, brompheniramine, cetirizine, chlorpheniramine, carebastine, descarboethoxyloratadine (also known as SCH-34117), diphenhydramine, ebastine, fexofenadine, loratadine, or norastemizole.

Representative combinations include: the $H_3$ antagonists of this invention with loratadine, $H_3$ antagonists of this invention with descarboethoxyloratadine, $H_3$ antagonists of this invention with fexofenadine, and $H_3$ antagonists of this invention with cetirizine.

Those skilled in the art will know that the term "upper airway" means the upper respiratory system—i.e., the nose, throat, and associated structures.

When used herein, unless indicated otherwise, the following terms have the given meanings:

lower alkyl (including the alkyl portions of lower alkoxy)—represents a straight or branched, saturated hydrocarbon chain having from 1 to 6 carbon atoms, preferably from 1 to 4;

aryl—represents a carbocyclic group having from 6 to 14 carbon atoms and having at least one benzenoid ring, with all available substitutable aromatic carbon atoms of the carbocyclic group being intended as possible points of attachment, said carbocyclic group being optionally substituted with 1 to 3 groups, each optional substituent being independently selected from the group consisting of lower alkyl, halogen, trihalomethyl, CN, $NO_2$, $OR^{10}$ or $NR^{10}R^{11}$, wherein $R^{10}$ and $R^{11}$ are independently selected from hydrogen, lower alkyl or trihalomethyl; preferred aryl groups include 1-naphthyl, 2-naphthyl and indanyl, and especially phenyl and substituted phenyl;

cycloalkyl—represents a saturated carbocyclic ring having from 3 to 8 carbon atoms, preferably 5 or 6, optionally substituted by 1 to 3 groups independently selected from the group consisting of lower alkyl trihalomethyl and $NR^{10}R^{11}$, wherein $R^{10}$ and $R^{11}$ are independently selected from hydrogen, lower alkyl or trihalomethyl; said cycloalkyl group optionally being fused to an aryl ring (e.g., phenyl), e.g., cyclohexyl fused to phenyl;

heterocyclic—represents saturated and unsaturated non-aromatic cyclic organic groups having at least one O, S and/or N atom interrupting a carbocyclic ring structure that consists of one ring or two fused rings, wherein each ring is 5-, 6- or 7-membered, which ring structure has from 2 to 8, preferably from 3 to 6 carbon atoms; e.g., 2- or 3-pyrrolidinyl, 2-, 3- or 4-piperidinyl, 2- or 3-piperazinyl, 2- or 3-morpholinyl, or 2- or 3-thiomorpholinyl; said heterocyclic group being optionally substituted by 1 to 3 groups independently selected from the group consisting of lower alkyl, trihalomethyl, and $NR^{10}R^{11}$, wherein $R^{10}$ and $R^{11}$ are independently selected from hydrogen, lower alkyl or trihalomethyl, said substituents being bound to carbon atoms (substitutable carbon atoms) in the ring such that the total number of substituents in the ring is 1 to 3; and wherein said heterocyclic ring contains nitrogen atoms, said nitrogen atoms (i.e., the substitutable nitrogen atoms) being optionally substituted with lower alkyl (e.g., alkyl), e.g., 1-N-methylpyrrolidinyl;

halogen—represents fluorine, chlorine, bromine and iodine; and heteroaryl—represents a cyclic organic group having at least one O, S and/or N atom interrupting a carbocyclic ring structure and having a sufficient number of delocalized pi electrons to provide aromatic character, with the aromatic heterocyclic group having from 2 to 14, preferably 4 or 5 carbon atoms, e.g., indolyl, 2-, 3- or 4-pyridyl, 2- or 3-furyl, 2- or 3-thienyl, 2-, 4- or 5-thiazolyl, 2- or 4-imidazolyl, 2-, 4- or 5-pyrimidinyl, 2-pyrazinyl, or 3- or 4-pyridazinyl, and the like; preferred heteroaryl groups are 2-, 3- and 4-pyridyl; said heteroaryl groups being optionally substituted with 1 to 3 groups, each optional substituent being independently selected from the group consisting of lower alkyl, halogen, trihalomethyl, CN, $NO_2$, $OR^{10}$ or $NR^{10}R^{11}$, wherein $R^{10}$ and $R^{11}$ are independently selected from hydrogen, lower alkyl or trihalomethyl, said substituents being bound to carbon atoms (substitutable carbon atoms) in the ring such that the total number of substituents in the ring is 1 to 3.

Compounds of this invention are antagonists of the $H_3$ receptor. As such, they may be useful for the treatment of various allergic, inflammatory, GI-tract, or cardiovascular diseases. In addition, they possess CNS activity; they may be useful as sleep regulators, anticonvulsants, cognition enhancers, antidepressants, regulators of hypothalamo-hypophyseal secretions, and the like.

Compounds of formula I include those compounds wherein $R^1$ is H.

Compounds of formula I also include compounds wherein n is 1.

Compounds of formula I further include compounds wherein $R^1$ is H and n is 1.

Compounds of formula I additionally include compounds wherein wherein $R^1$ is H, $R^7$ is H, and n is 1.

In addition, compounds of formula I include compounds wherein $R^{15}$ is hydrogen.

Preferred compounds of formula I are compounds of the formulae II, III, IV, V, VI, and VII described below.

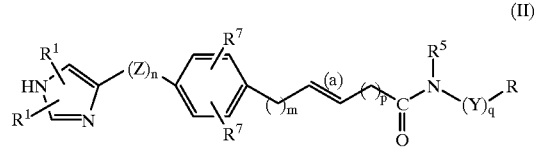

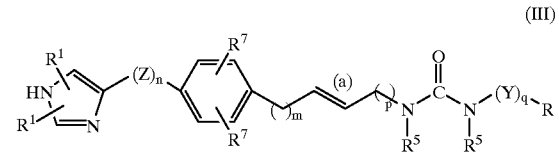

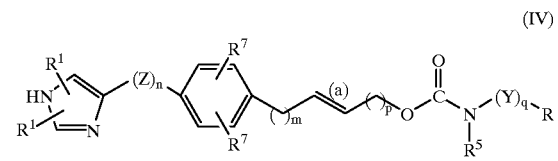

-continued

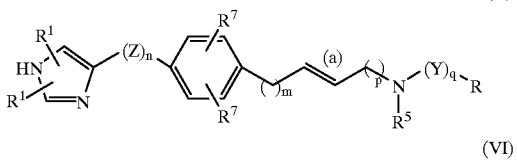
(V)

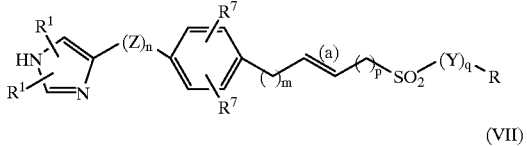
(VI)

(VII)

wherein $R^1$, $R^7$, R, Y, Z, (a), m, n, p and q are as defined for formula I.

$R^1$, $R^7$ and $R^{15}$ are hydrogen. More preferably, n is 1, and $R^1$, $R^7$ and $R^{15}$ are hydrogen. Particularly preferred are those compounds wherein n is 1, and $R^1$, $R^7$ and $R^{15}$ are hydrogen, and R is phenyl, pyridyl, substituted phenyl or substituted pyridyl. The preferred substituents in said phenyl or pyridyl groups are halogen, preferably chlorine or fluorine, methoxy, trifluoromethyl, CN or trifluoromethoxy. Preferably there are one or two of said substitutents, and each substituent is independently selected.

For compounds of formula II, m is preferably 0. Most preferred are those compounds of formula II wherein m and p are both 0; q is 0 or 1, and, when q=1, Y is —$CHR^5CHR^5$— with one $R^5$ being hydrogen and the other as defined for $R^5$ above. For formulae III and IV m is preferably 0 or 1, p is 1 or 2 and q is 0. For all the above groups of compounds the preferred meaning of R is phenyl or phenyl substituted by one or two of the substituents described above in the definition of aryl. The most preferred substituents are CN, chlorine and fluorine, with chlorine and fluorine being more preferred. Preferred R-groups are those wherein there is one substituent in the 3-or 4-position, e.g., 4-Cl-phenyl or 3-F-phenyl. If there are two substituents, then the 3,5-substituted compounds are preferred. The preferred meaning of $R^5$ is hydrogen. Most preferred are compounds of formula II.

PREPARATION OF FINAL PRODUCTS

Compounds of the formula I can be prepared by standard methods known in the art. Typical methods appropriate for the preparation of the compounds of the formula I are illustrated below. In the reaction schemes below only one $R^1$ or one $R^7$ group is shown; however, compounds having the other two groups (i.e., the other $R^1$ and $R^7$) can also be made by the reactions described below. The particular process chosen should not cause significant decomposition elsewhere in the molecule; for example, removal of a protecting group by hydrogenolysis should not cause the loss of an essential phenylmethyl group.

Basically well known processes such as those described in WO 95/14007 referred to above can, with some modifications, depending on the nature of the group X, be used. The general aspect of the processes for making the final compounds can be illustrated by the following reaction scheme:

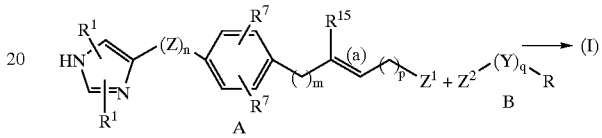

$R^1$, $R^7$, $R^{15}$, R, Y, Z, (a), n, m, p and q are as defined for formula I, and $Z^1$ and $Z^2$ are reactive groups selected in such a manner that they provide the group X in the final compound. Obviously certain groups may have to be protected during the reaction(s). This applies in particular to the NH-group in the imidazole ring. Standard procedures for protection and de-protection may be used.

Starting compounds of formulas A and B are either known or may be prepared according to well known procedures. Reactions 1, 2 and 3 below illustrate the preparation of such compounds.

Reaction 1 (n=1)

For n=1, a metal derivative of an N-protected imidazole (wherein M is e.g., MgBr or MgI, and Pg represents a suitable protecting group, such as, triphenylmethyl) can be reacted with a $Z^3$-substituted-benzaldehyde of the formula IX, and the resulting substituted benzyl alcohol can be reduced, for example, as indicated in the following scheme:

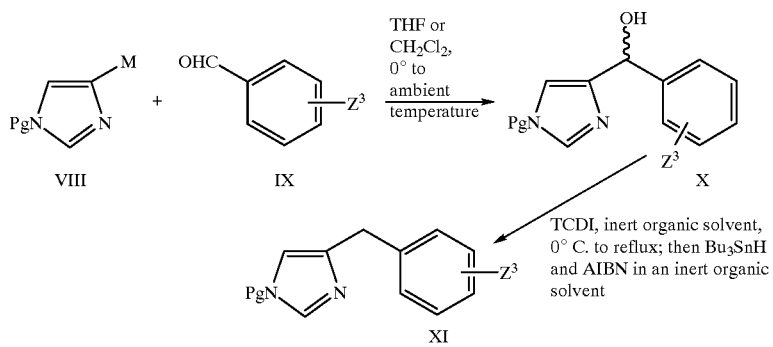

Reaction 2 (n=1)

A further method is illustrated in the reaction scheme below. A solution of sodium bis(trimethylsilyl)amide in THF cooled to 0° C. is treated with triethylphosphonoacetate. Terephthalaldehyde mono-(diethyl acetal) dissolved in THF is added. The reaction mixture is stirred at 30–40° C. for 3–4 h and concentrated. The residue is washed with H$_2$O and brine, dried and concentrated to give the crude desired compound which is then purified. Tr represents trityl.

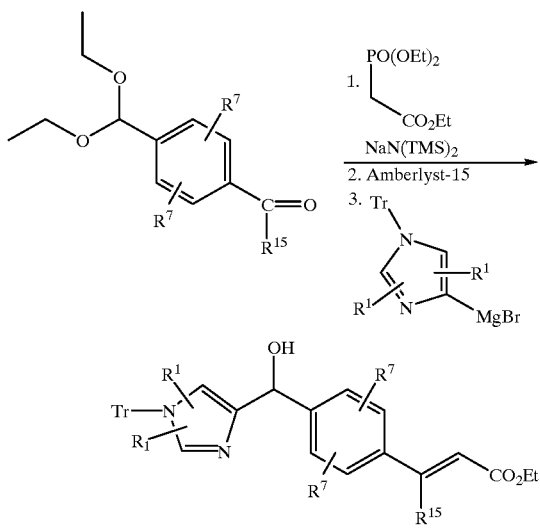

Reaction 3 (n=2)
For n=2, the following scheme can be used:

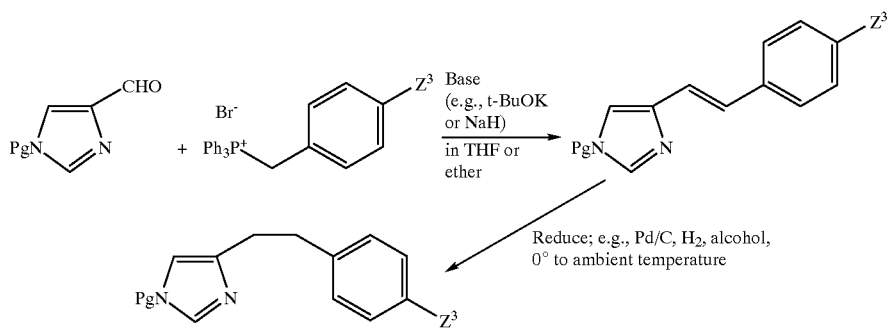

In the above reaction schemes, wherein the substituents R$^1$ and R$^7$ were not included in the formulas, it will be apparent to those skilled in the art that starting compounds wherein such substituents are present could also be used in the reactions described.

Z$^3$ represents a group —(CH$_2$)$_m$—CR$^{15}$=CH—(CH$_2$)$_p$—Z$^1$ or a group which may be converted into such a group. Ph represents a phenyl group. Other procedures for making compounds of formula A may be found in WO 95/14007. In the following reaction schemes some procedures for preparing the appropriate Z$^3$ group are shown. Additional examples are found in WO 95/14007.

The final compounds of this invention are then prepared by reacting a compound A with a compound B followed by the removal of any protecting groups. Such reactions are illustrated in the reaction schemes below. (R$^6$ represents the group —(Y)$_q$—R).

In the reaction schemes below, J represents (Z)$_n$.

Reaction 4—Carbamates

Step 1

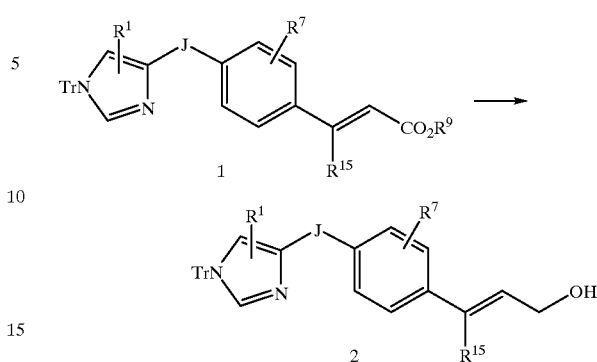

In Step 1, the ester 1 is dissolved in a suitable solvent such as THF, ether, dioxane, toluene or methylene chloride, preferably THF, and is treated with a reducing agent such as lithium aluminum hydride or diisobutylaluminum hydride, preferably diisobutylaluminum hydride, at a temperature of from −20° C. to about 50° C., preferably 0° C., to give the alcohol 2. R$^9$ is lower alkyl Step 2

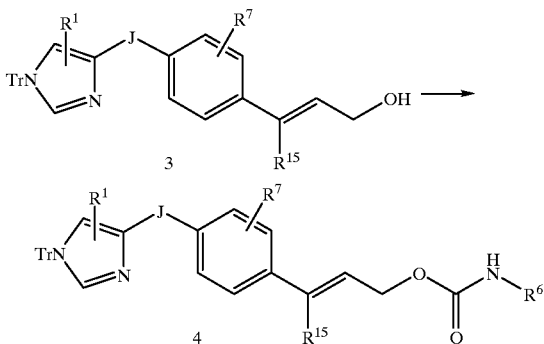

In Step 2, the alcohol 2 is dissolved in a suitable solvent such as THF, ether, dioxane, toluene or methylene chloride, preferably THF, and is treated with an isocyanate R$^6$NCO in the presence of a base such as triethylamine or the like at a temperature of from −20° C. to 50° C. to yield the carbamate 4.

Step 3

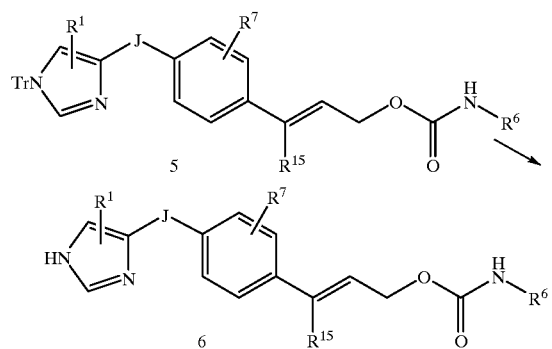

In Step 3, a solution of the carbamate 5 in a suitable alcoholic solvent such as methanol or ethanol, preferably methanol, is treated with a dilute solution of a mineral acid such as HCl in methanol at a temperature of from 20° C. to 100° C., preferably 60° C., to give the product 6.

Reaction 5—Esters

Step 1

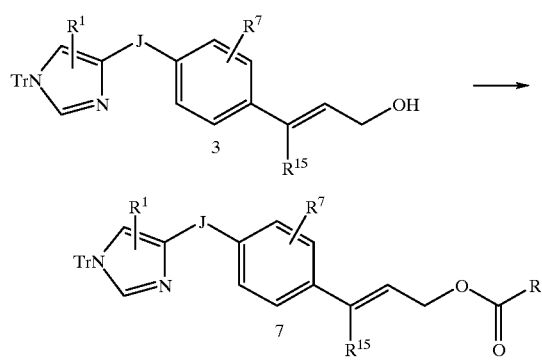

In Step 1 the alcohol 3 is reacted with an acid chloride, $R^6C(O)Cl$ in an inert solvent such as ether, THF, dioxane, or methylene chloride, preferably methylene chloride, in the presence of a tertiary amine base such as triethylamine at a temperature of from 0° C. to 50° C., preferably 0° C., to give the product 7.

Step 2

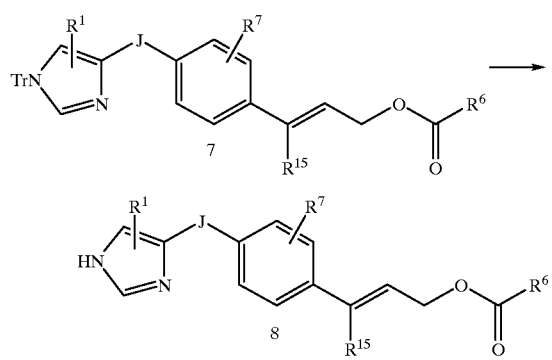

In an analogous manner to that described above, compound 7 is transformed to compound 8.

Reaction 6—Ethers

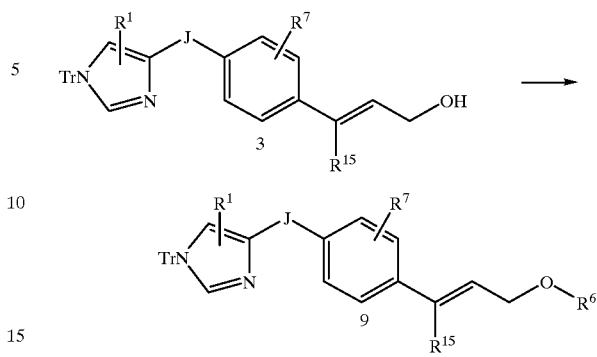

A solution of alcohol 3 in a suitable solvent such as THF or dioxane, preferably THF is added to a suspension of a hydride base such as NaH or KH, preferably NaH, in THF at a temperature of from 0° C. to 50° C., preferably 0° C. The reaction is allowed to warm to room temperature for a suitable time to complete alkoxide formation. A suitable alkylating agent, $R^6L$ is added and the reaction stirred for a suitable period of time to complete the reaction. Suitable leaving groups L include Cl, Br, I, and activated forms of OH such as $OSO_2CF_3$. Other strong bases can include lithium diisopropylamide and lithium or sodium bistrimethylsilylamide. Deprotection as described above provides the desired compound.

Reaction 7—Amines

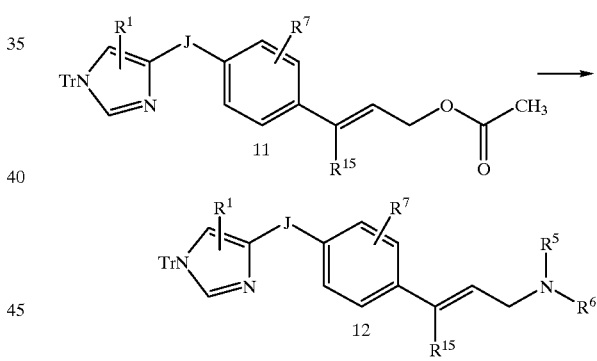

A solution of the acetate 11 and an amine $R^5R^6NH$ in a suitable solvent such as THF, dioxane, toluene, DMF or the like, preferably THF, is treated with a suitable palladium catalyst such as tetrakis(triphenylphosphine)-palladium at a temperature of from 0° C. to about 100° C., preferably 65° C. to give the amine 12. Deprotection as above gives the amine.

Reaction 8—Amines

Step 1

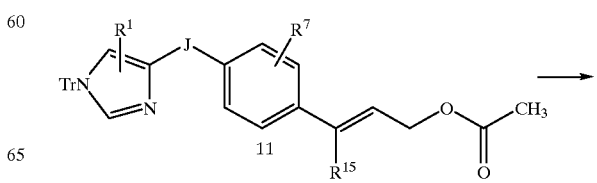

-continued

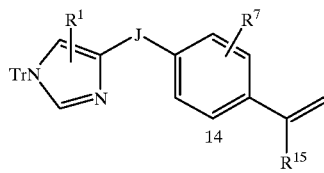

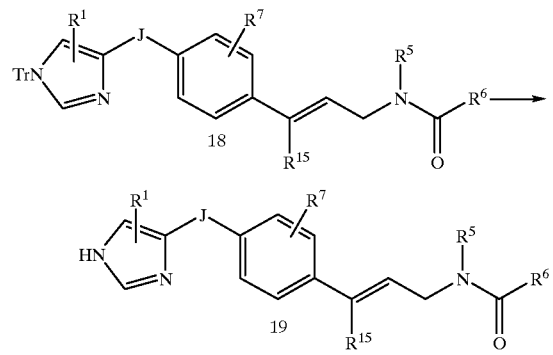

The acetate 11 is treated in an analogous manner to that above substituting trimethylsilylazide for the amine $R^5R^6NH$ to give an allylic azide. Alternatively, instead of trimethylsilylazide, 11 can be treated with $NaN_3$ in a THF/water mixture in the presence of a palladium catalyst to give the azide. In part 2, the azide is reduced to the amine 14 by dissolution in a suitable organic solvent such as methanol or ethanol, preferably ethanol, adding a hydrogenation catalyst such as Pd/C, $PtO_2$, or Raney Ni, preferably Pd/C, and hydrogenating under an atmosphere of hydrogen (16–60 psi, preferably 60 psi) to give 14. Other reduction methods that can serve equally well include treatment of the azide with $NaBH_4$, $LiBH_4$, $LiAlH_4$, or the like, or with a tertiary phosphine in a water/THF mixed solvent system.

Step 2

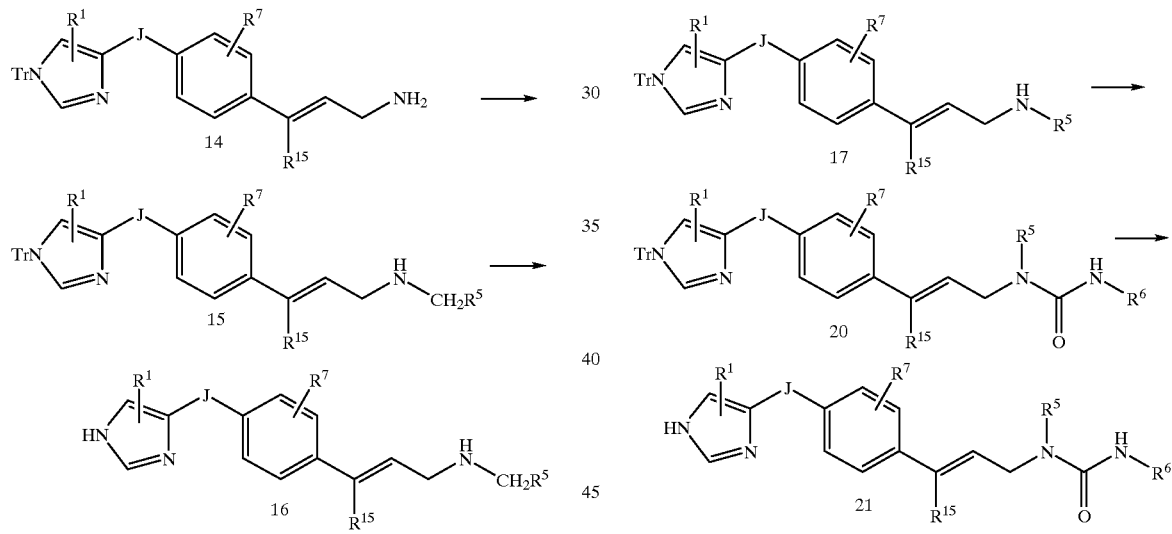

In Step 2, the amine 14 is dissolved in a polar solvent such as methanol, ethanol, or trifluoroethanol and treated with an aldehyde $R^5CHO$ or ketone $(R^5)_2CO$ in the presence of powdered molecular sieves at a temperature of from 0° C. to 80° C., preferably 22° C. for a time sufficient to ensure imine formation. A reducing agent such as $NaBH_3CN$ or $Na(AcO)_3BH$, preferably $Na(AcO)_3BH$, is added and the reaction stirred until complete. Deprotection of the amine 15 gives the product 16.

Reaction 9—Amides

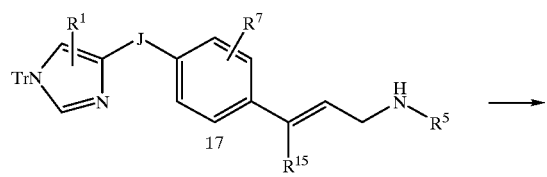

The reactions can be run in a manner analogous to that described for preparing the ester above to give the product 19. Alternatively, the amine 17 can be coupled with a carboxylic acid $R^6CO_2H$ by treating a solution of 17 in an inert solvent such as methylene chloride with EDCI, HOBT, NMM, and the acid at a temperature of from 0° C. to 80° C. preferably 22° C.

Reaction 10—Ureas

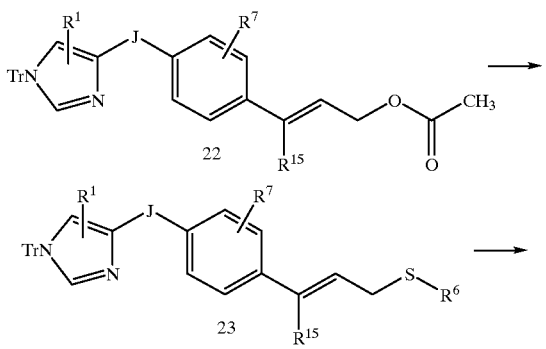

These reactions are run in a manner analogous to Step 2 and 3 of the reactions for preparing the carbamates above.

Reaction 11—Sulfides

-continued

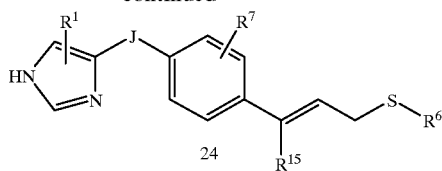

The acetate 22 is reacted with a thiol R⁶SH in a manner similar to that described above for the synthesis of an amine from the acetate to give the sulfide 23 which is deprotected to give the product 24.

Reaction 12—Sulfones

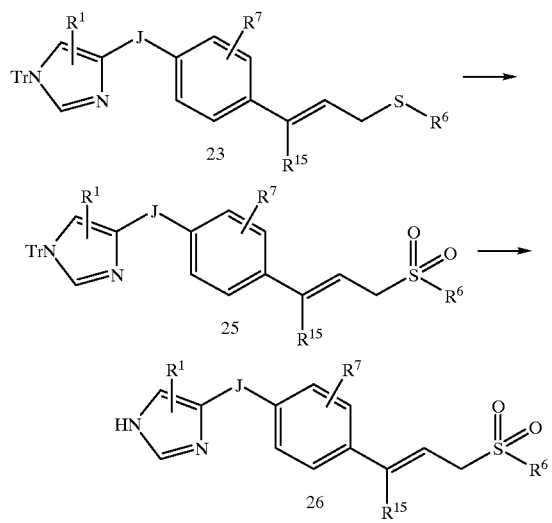

The sulfide 23 is reacted with a suitable oxidizing agent such as m-CPBA or oxone, preferably oxone, in a suitable organic solvent at a temperature of from 0° C. to 80° C., preferably 22° C., to give the sulfone 25. Compound 25 is deprotected to give the product Reaction 13— —S(O)NR⁵—

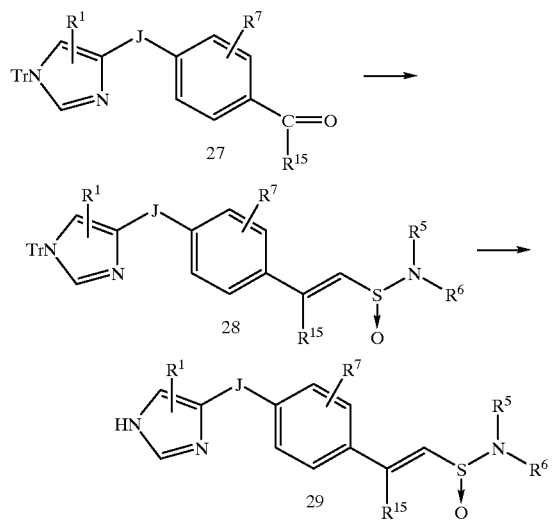

The aldehyde 27 is treated in a similar manner to that described in *Gazz. Chim. Ital.* 1991, 121, 471 to afford the vinyl sulphenamide 28. Compound 28 is then deprotected to give the target 29.

Reaction 14— —SO₂—

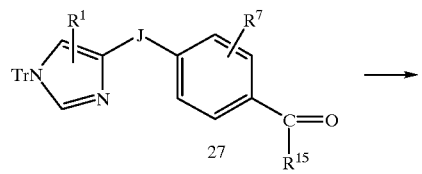

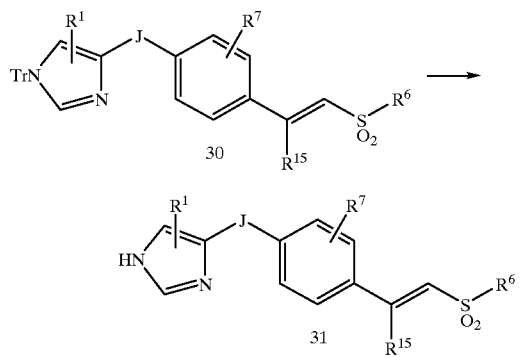

The aldehyde 27 is treated in a similar manner to that described in *Ind. J. Chem., Sec B* 1982, 21B, 208 to afford the vinyl sulphone 30. Compound 30 is then deprotected to give the target 31.

Reaction 15— —SO₂ NR⁵—

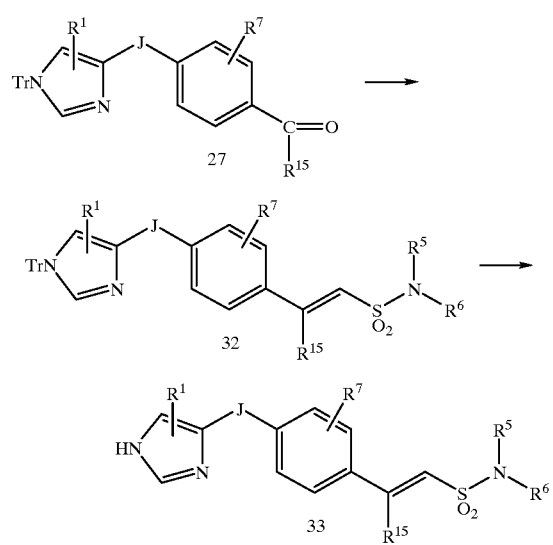

The aldehyde 27 is treated in a similar manner to that described in *Synthesis* 1975, 321 to afford the vinyl sulphonamide 32. Compound 32 is then deprotected to give the target 33.

Reaction 16— —C(NH)NR⁵—

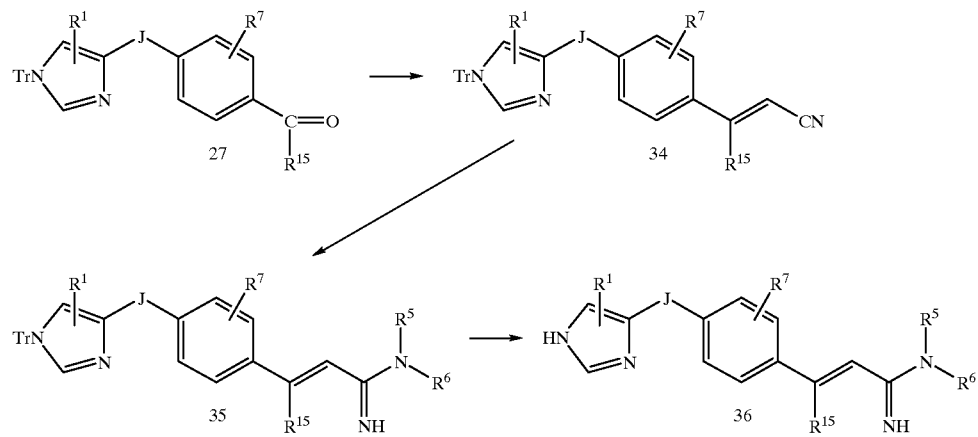

A solution of diethyl- or dimethylcyanomethyl phosphonate in a suitable organic solvent such as THF, ether, or dioxane, preferably THF, is treated with a strong base such as lithium diisopropylamide, or lithium, sodium or potassium bis(trimethylsilyl)amide at a temperature of from −25° C. to about 50° C., preferably 0° C. After 1 hr, the phosphonate carbanion is treated with a solution of the aldehyde 27 in the same solvent. The reaction is stirred at a temperature suitable to complete the reaction and give 34.

Compound 34 is then reacted with the reagent formed by combining equimolar amounts of trimethylaluminum and a suitable amine $R^5R^6NH$ in an inert organic solvent such as toluene or xylene, preferably toluene, at a temperature of from 20° C. to 130° C. preferably 90° C. to give compound 35.

Deprotection of compound 35 gives the product 36.

Reaction 17— —CONR⁵—

In this reaction scheme K represents $(Z)_{n-1}$.

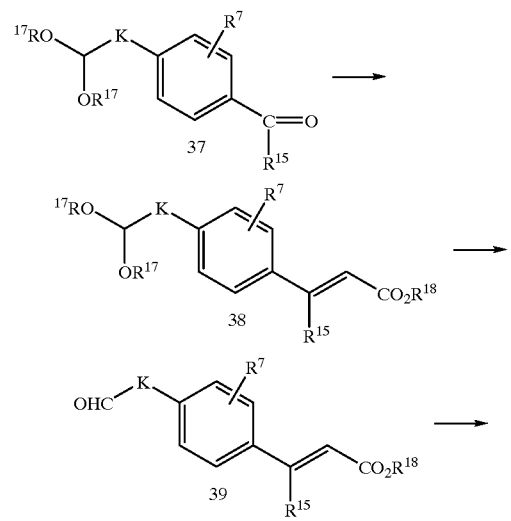

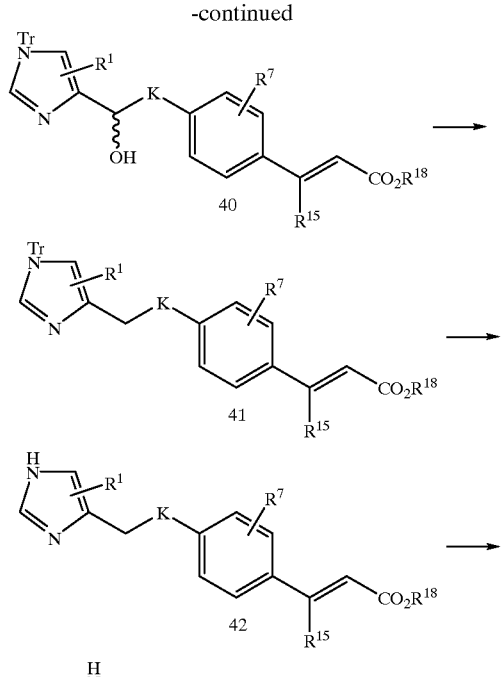

wherein $R^{18}$ is lower alkyl, and $R^{17}$ is lower alkyl or the two $R^{17}$ groups together with the oxygen atoms to which they are bound form a 5 or 6 membered ring.

Triethylphosphonoacetate is treated with a strong base such as LDA or lithium, sodium or potassium bis (trimethylsilyl)amide in an ethereal solvent such as THF, ether, or dioxane, preferably THF, at a temperature from −20° C. to 50° C., preferably 0° C. The phosphonate stabilized carbanion is then treated with the carbonyl compound 37 and the mixture stirred at room temperature until the reaction is complete. Other suitable bases include NaH or KH in a polar aprotic solvent such as DMSO or DMF. The product 38 is then deprotected as described above to give the aldehyde 39.

The imidazole compound obtained by the reaction

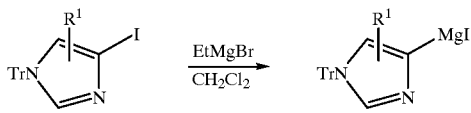

is then reacted with the aldehyde 39 to give 40 which is reduced to compound 41. Deprotection provides the compound 42 which is then reacted with the amine NHR[5] R[6] to give the final compound 43.

Compounds useful in this invention are exemplified by the following examples, which should not be construed to limit the scope of the disclosure.

EXAMPLE 1

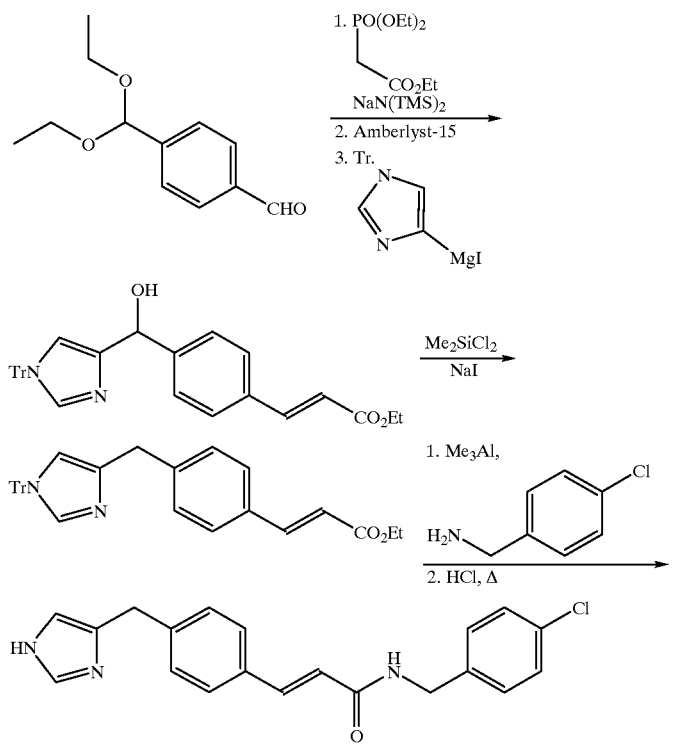

Step 1

A solution of 1 M sodium bis(trimethylsilyl)amide in THF (110 ml, 110 mmol) cooled to 0° C. was treated with triethylphosphonoacetate (23.5 ml, 118 mmol). After 20 min. the reaction mixture was warmed to RT. and terephthalaldehyde mono-(diethyl acetal) (19.3 ml, 97.0 mmol) dissolved in THF (250 ml) was added over 25 min. The reaction mixture was stirred at 35° C. for 3.5 h and concentrated. The residue was suspended in EtOAc (250 ml), washed with $H_2O$ (100 ml) and brine (100 ml), dried with $MgSO_4$ and concentrated to give 27 g of crude intermediate.

The crude intermediate (27 g) was dissolved in acetone (350 ml) and $H_2O$ (4.5 ml), treated with Amberlyst-15 resin (3.1 g) for 2.5 h, filtered and concentrated to give the aldehyde intermediate.

To a cooled (0° C.) solution of 4-iodo-1-trityl imidazole (41.3 g, 96.9 mmol) in $CH_2Cl_2$ (500 ml) was added 3M EtMgBr (35 ml, 105 mmol) over 15 min. After 30 min. at 0° C. the reaction mixture was warmed to RT. and a solution of the aldehyde intermediate in $CH_2Cl_2$ (50 ml) was added. After 2 h, the reaction mixture was added to 1 L of half sat. aqueous $NH_4Cl$. The organic layer was partitioned off and the aqueous layer was extracted with $CH_2Cl_2$ (3×200 ml). The combined organic layers were washed with brine (250 ml), dried with $MgSO_4$ and concentrated. The product was purified by silica gel chromatography eluting with 1:1 $CH_2Cl_2$-EtOAc to give 30.2 g of product (59 mmol, 61% overall yield): $^1$H-NMR (CDCl$_3$) δ 1.34 (t, J=7.1 Hz, 3H), 4.26 (q, J=7.1 Hz, 2H), 5.79 (s, 1H), 6.40 (d, J=16.0 Hz, 1H), 6.59 (s, 1H), 7.1–7.5 (m, 20H), 7.65 (d, J=16.0 Hz, 1H).

Step 2

To a solution of the product from Step 1 (10.2 g, 19.9 mmol), $CH_2Cl^2$ (115 ml), acetone (115 ml) and NaI (11.9 g, 79.3 mmol) was added dichlorodimethylsilane (19.4 ml, 159 mmol). After 15 min. the reaction mixture was added to $CH_2Cl_2$ (600 ml) and washed with 10% aqueous sodium thiosulfate (5×400 ml), $H_2O$ (2×400 ml) and brine (400 ml), dried with $MgSO_4$ and concentrated. The product was purified by silica gel chromatography eluting with 2:1 followed by 1:1 $CH_2Cl_2$-EtOAc to give 7.2 g of product (14 mmol, 72% yield). $^1$H-NMR (CDCl$_3$) δ 1.33 (t, J=7.0 Hz, 3H), 3.90 (s, 2H), 4.26 (q, J=7.0, 2H), 6.39 (d, J=16.0 Hz,1H), 6.58 (s, 1H), 7.1–7.5 (m, 20H), 7.65 (d, J=16.0 Hz, 1H).

Step 3

To a cooled (0° C.) solution of 4-chlorobenzylamine (61 ml, 0.50 mmol) in toluene (2.0 ml) was added 2M trimethyl aluminum in toluene (1.0 ml, 2.0 mmol) in toluene (10 ml) and stirred at RT. for 45 min. To the reaction mixture was added a solution of the product from step 2 (0.25 g, 0.50 mmol) in toluene (5.0 ml). After heating at 65° C. for 3.5 h, the reaction mixture was cooled, carefully quenched with sat. Na$_2$SO$_4$ (aq.), concentrated and purified by silica gel chromatography eluting with 5% NH$_3$ sat. MeOH in CH$_2$Cl$_2$ to give 0.14 g of the amide intermediate (0.23 mmol, 46% yield).

A solution of the amide intermediate (0.14 g, 0.23 mmol) in EtOH (5.0 ml) was treated with 3M HCl (5.0 ml) at 65° C. for 3 h and concentrated. Purification by silica gel chromatography eluting with 5% NH$_3$ sat. MeOH in CH$_2$Cl$_2$ followed by acidification with 3M HCl and concentration gave 42 mg of the titled product (0.11 mmol, 48% yield). HRMS (M+H$^+$): m/e calc'd [C$_{20}$H$_{19}$N$_3$OCl]$^+$: 352.1217, found 352.1218.

EXAMPLE 2
Step 1

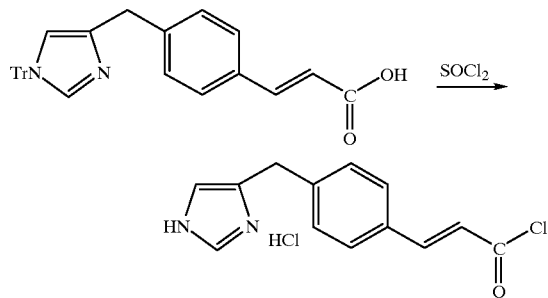

The acid was suspended in SOCl$_2$ (20 ml) and stirred for 20 hours at room temperature. The excess SOCl$_2$ was removed under reduced pressure and the residue dried by azeotropic removal of toluene. The resulting yellow solid was used directly in the next step without purification.

Step 2

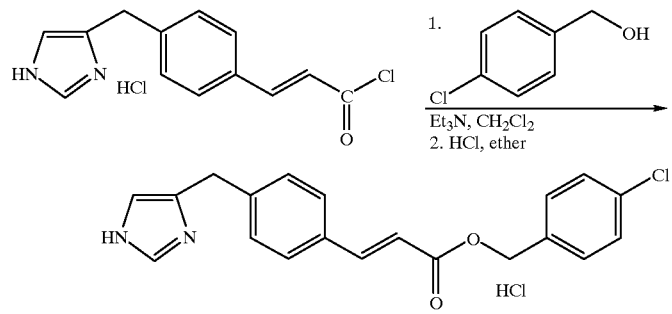

4-Chlorobenzyl alcohol (0.71 g, 5 mmol) and triethylamine (1.01 g, 10 mmol) were added to a suspension of the acid chloride from Step 1 in dry methylene chloride (15 ml) at 0° C. The reaction mixture was warmed to room temperature and stirred for 24 hours. Additional methylene chloride (50 ml) was added and the organic layer was washed with saturated aqueous NaHCO$_3$. The organic layer was separated and dried (MgSO$_4$). Concentration gave an amber oil that was purified on a flash column (97:3 CH$_2$Cl$_2$:MeOH/NH$_3$). A white solid was obtained (0.36 g, 46% from nitrile 4). This material was dissolved in methylene chloride (10 ml) and 1N HCl in ether (5 ml) was added. The solvent was evaporated under a stream of dry argon to give the compound as a white solid.

EXAMPLE 3
Step 1

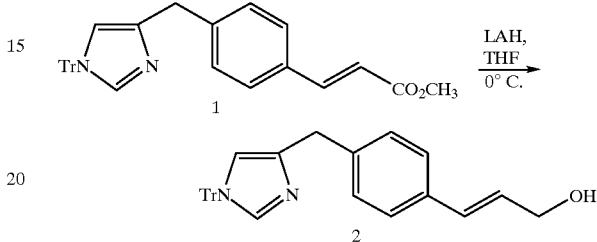

Treat a solution of 1(4.84 gr., 10 mmol) in dry THF (50 ml) at 0° C. and under a nitrogen atmosphere with a solution of LAH in THF (12.5 ml of a 1 M solution, 12.5 mmol). Stir the reaction until TLC indicates the reaction is complete. Dilute the reaction with ether (50 ml) and quench by the addition of saturated aqueous Na$_2$SO$_4$. After drying with solid Na$_2$SO$_4$, the mixture can be filtered, concentrated, and purified via flash column chromatography to give the product 2.

Step 2

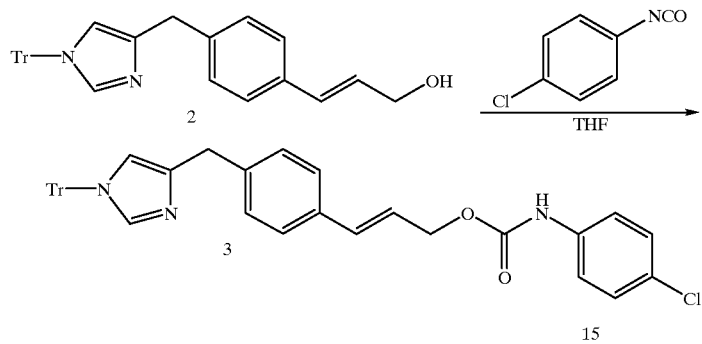

Stir a solution of the alcohol 2 (2.28 gm., 5 mmol) and the isocyanate (0.92 gm., 6 mmol) in dry THF (25 ml) under a nitrogen atmosphere until TLC indicates that the reaction is complete. Remove the THF under reduced pressure, and purify the residue via flash column chromatography to give the product 3.

Step 3

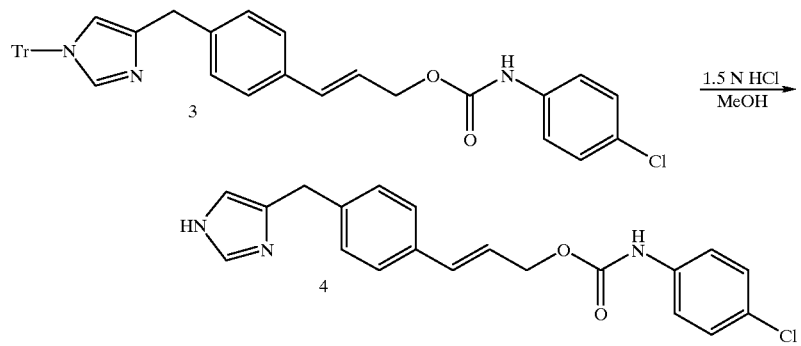

In a manner similar to that described in Example 1, compound 3 (1 gm., 1.6 mmol) may be converted into the product 4.

EXAMPLE 4

Step 1

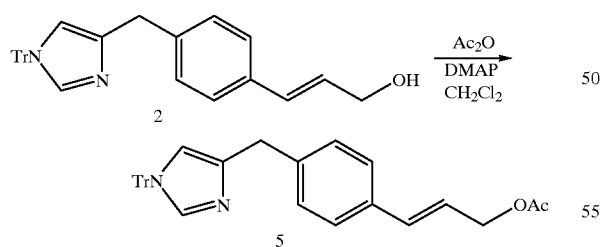

Treat a solution of the alcohol 4 (2.28 gm., 5 mmol) and DMAP (61 mg, 0.5 mmol) in dry methylene chloride (20 ml) at 0° C. under a nitrogen atmosphere with acetic anhydride (0.61 gm, 6 mmol). Stir the reaction until TLC indicates that it is complete. Dilute the reaction with additional methylene chloride (50 ml) and wash with saturated aqueous $NaHCO_3$, brine and dry ($MgSO_4$). Filtration and concentration under reduced pressure gives a residue that can be purified via flash column chromatography to yield the product.

Step 2

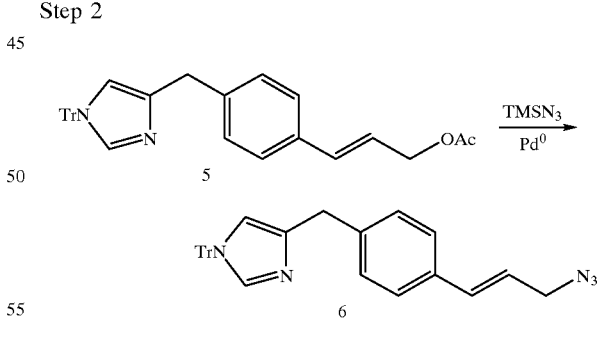

Stir a mixture of dipalladium tris(dibenzylidine acetone) (92 mg, 0.1 mmol), triphenylphosphine (210 mg, 0.8 mmol), trimethylsilyl azide (690 mg, 6 mmol) and compound 5 (1.92 gm, 4 mmol) in dry THF (20 ml) under nitrogen at 50° C. until TLC indicates the reaction is complete. Concentration under reduced pressure gives a residue that can be purified via flash column chromatography to yield the product 6.

Step 3

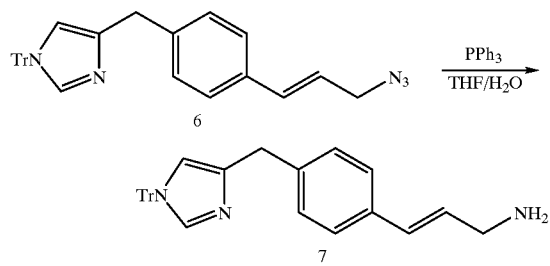

Treat a solution of the azide 6 (1.44 gm, 3 mmol) in THF (10 ml) with triphenylphosphine (0.77 gm, 3 mmol) and water (81 mg, 4.5 mmol) and stir until TLC indicates the reaction is complete. The solvent can be removed under reduced pressure and the residue can be purified via flash column chromatography to yield the product 7.

Steps 4 and 5

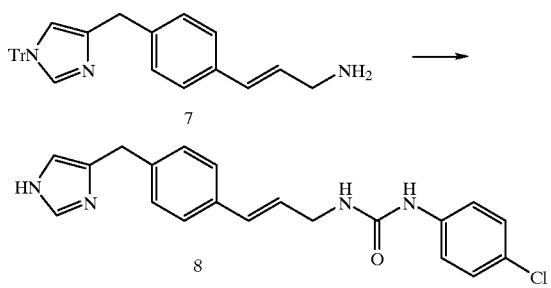

In a manner similar to that described in Example 2 Steps 2 and 3, compound 7 (0.46 gm, 1 mmol) may be converted to the product 8.

EXAMPLE 5

Step 1

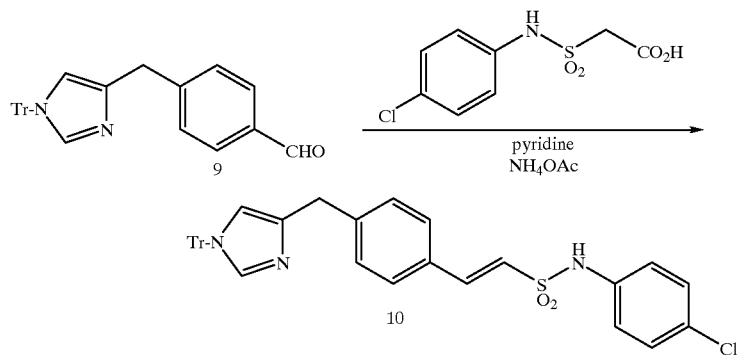

Heat compound 9 (2.14 gm, 5 mmol), ammonium acetate (100 mg), and the sulfonylacetic acid reagent (synthesized according to the procedure described in *Synthesis*, 1975, 321; 1.05 gm, 4.2 mmol) at reflux until TLC indicates the reaction is complete. Dilute with methylene chloride (100 ml) and wash with dilute HCl, aqueous NaHCO$_3$, water, brine and dried (MgSO$_4$). After filtration and concentration under reduced pressure, the residue can be purified via flash column chromatography to yield the product 10.

Step 2

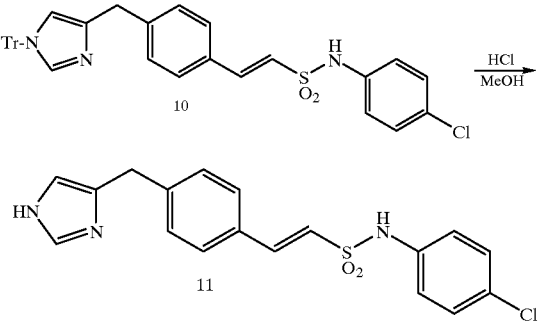

In a manner similar to that described in Example 2 Step 3, compound 10 (0.62 gm, 1 mmol) may be converted to the product 11.

Following the procedures outlined above the compounds ("Com") of formula IA:

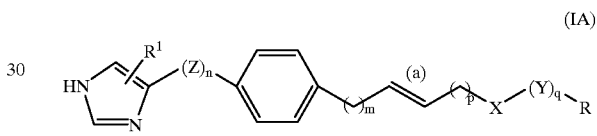

may be prepared wherein the substituents are defined in the table below. In the table R$^1$ represents the substituent on the imidazole ring. R$^1$ for the (Z)$_n$ group is H.

| Com. No. | n | m | p | q | Y | X | R | R¹ |
|---|---|---|---|---|---|---|---|---|
| 1 | 1 | 0 | 0 | 0 | — | CONH | 4-chlorophenyl | H |
| 2 | 1 | 0 | 0 | 1 | CH$_2$ | CONH | 4-chlorophenyl | H |
| 3 | 1 | 0 | 0 | 1 | CH$_2$CH$_2$ | CONH | 4-chlorophenyl | H |
| 4 | 1 | 0 | 0 | 0 | — | CON(CH$_3$) | 4-chlorophenyl | H |
| 5 | 1 | 0 | 0 | 1 | CH$_2$CH$_2$ | CON(CH$_3$) | 4-chlorophenyl | H |
| 6 | 1 | 0 | 0 | 0 | — | CONH | phenyl | H |
| 7 | 1 | 0 | 0 | 0 | — | CONH | cyclohexyl | H |
| 8 | 1 | 0 | 0 | 1 | —CH$_2$CH$_2$— | CONH | 3-chlorophenyl | H |
| 9 | 1 | 0 | 0 | 1 | CH(CH$_3$)CH$_2$ | CONH | 4-chlorophenyl | H |
| 10 | 1 | 0 | 0 | 1 | CH$_2$CH(CH$_3$) | CONH | phenyl | H |
| 11 | 1 | 0 | 0 | 1 | CH$_2$CH$_2$ | CONH | 4-methoxy-phenyl | H |
| 12 | 1 | 0 | 0 | 1 | CH$_2$CH$_2$ | CONH | 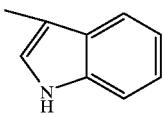 | H |
| 13 | 1 | 0 | 0 | 0 | — | CONH | 4-chlorophenyl | 1-CH$_3$ |
| 14 | 1 | 0 | 0 | 0 | — | CONH | 3-chlorophenyl | 1-CH$_3$ |
| 15 | 1 | 0 | 0 | 1 | CH$_2$CH$_2$ | CONH | 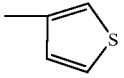 | H |
| 16 | 1 | 0 | 0 | 1 | CH$_2$CH$_2$ | CONH | 3-fluorophenyl | H |
| 17 | 1 | 0 | 0 | 1 | CH$_2$CH$_2$ | CONH | 3-pyridyl | H |
| 18 | 1 | 0 | 0 | 1 | CH$_2$CH$_2$ | CONH | 2-fluorophenyl | H |
| 19 | 1 | 0 | 0 | 1 | CH$_2$CH$_2$ | CONH | 2-chlorophenyl | H |
| 20 | 1 | 0 | 0 | 1 | CH$_2$CH$_2$CH$_2$ | CONH | 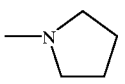 | H |
| 21 | 1 | 0 | 0 | 1 | CH$_2$ | CONH | 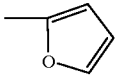 | H |
| 22 | 1 | 0 | 0 | 1 | CH$_2$CH$_2$ | CONH | 4-methyl-phenyl | H |
| 23 | 1 | 0 | 0 | 1 | CH$_3$<br>\|<br>CH(CH$_2$)$_2$ | CONH | phenyl | H |
| 24 | 1 | 0 | 0 | 0 | — | CONH |  | H |
| 25 | 1 | 0 | 0 | 0 | — | CO | 4-chlorophenyl | H |
| 26 | 1 | 0 | 0 | 1 | CH$_2$ | CONH | 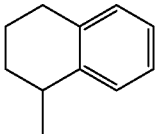 | H |
| 27 | 1 | 0 | 0 | 1 | CH$_2$CH$_2$ | CONH | 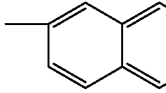 | H |
| 28 | 1 | 0 | 0 | 1 | CH$_2$CH$_2$ | CONH | 2m4-dichloro- | H |

-continued

| Com. No. | n | m | p | q | Y | X | R | R¹ |
|---|---|---|---|---|---|---|---|---|
| | | | | | | | phenyl | |
| 29 | 1 | 0 | 0 | 1 | CH²CH₂ | CONH | phenyl | H |
| 30 | 1 | 0 | 0 | 0 | — | CONH | 3,5-dichloro-phenyl | H |
| 31 | 1 | 0 | 0 | 0 | — | CONH | 3-chlorophenyl | H |
| 32 | 1 | 0 | 0 | 0 | — | CONH | 3-cyanophenyl | H |
| 33 | 1 | 0 | 0 | 0 | — | CONH | 3-methoxy-phenyl | H |
| 34 | 1 | 0 | 0 | 0 | — | CONH | 3,5-dimethyl-phenyl | H |
| 35 | 1 | 0 | 0 | 0 | — | CONH | 3-fluorophenyl | H |
| 36 | 1 | 0 | 0 | 0 | — | CONH | 4-fluorophenyl | H |
| 37 | 1 | 0 | 0 | 0 | — | CONH | 3-trifluoro-methoxy-phenyl | H |
| 38 | 1 | 0 | 0 | 0 | — | CONH | 4-trifluoro-methoxy-phenyl | H |
| 39 | 1 | 0 | 1 | 0 | — | NHCONH | 3,5-dimethyl-phenyl | H |
| 40 | 1 | 0 | 1 | 0 | — | NHCONH | 3-fluorophenyl | H |
| 41 | 1 | 0 | 1 | 0 | — | NHCONH | 4-fluorophenyl | H |
| 42 | 1 | 0 | 1 | 0 | — | NHCONH | 3-trifluoro-methoxy-phenyl | H |
| 43 | 1 | 1 | 1 | 0 | — | NHCONH | 4-trifluoro-methoxy-phenyl | H |
| 44 | 1 | 1 | 1 | 0 | — | NHCONH | 3-methoxy-phenyl | H |
| 45 | 1 | 1 | 1 | 0 | — | NHCONH | 3,5-dimethyl-phenyl | H |
| 46 | 1 | 1 | 1 | 0 | — | NHCONH | 3-fluorophenyl | H |
| 47 | 1 | 1 | 1 | 0 | — | NHCONH | 4-fluorophenyl | H |
| 48 | 1 | 1 | 1 | 0 | — | NHCONH | 3-trifluoro-methoxy-phenyl | H |
| 49 | 1 | 0 | 1 | 0 | — | NHCONH | 4-trifluoro-methoxy-phenyl | H |
| 50 | 2 | 0 | 1 | 1 | CH₂ | OCONH | 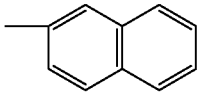 | H |
| 51 | 2 | 1 | 1 | 1 | CH₂CH₂ | OCONH | 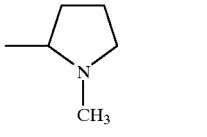 | H |
| 52 | 1 | 0 | 1 | 1 | CH₂CH₂ | OCONH | 2,4-dichloro-phenyl | H |
| 53 | 1 | 0 | 1 | 1 | CH₂CH₂ | OCONH | phenyl | H |
| 54 | 1 | 0 | 0 | 0 | — | COO | 3-methoxy-phenyl | H |
| 56 | 1 | 0 | 0 | 0 | — | N(CH₃) | 3,5-dimethyl-phenyl | H |
| 57 | 1 | 0 | 0 | 0 | — | NH | 3-fluorophenyl | H |
| 58 | 1 | 0 | 0 | 0 | — | SO₂NH | 4-fluorophenyl | H |
| 59 | 1 | 0 | 0 | 0 | — | C(NH)NH | 3-trifluoro-methoxy-phenyl | H |
| 60 | 1 | 0 | 0 | 0 | — | S | 4-trifluoro-methoxy-phenyl | H |
| 61 | 1 | 0 | 0 | 0 | — | CONH | 4-chlorophenyl | H |
| 62 | 1 | 0 | 0 | 0 | — | C(NH)NH | 4-chlorophenyl | H |

Also, following the above procedures compound 63:

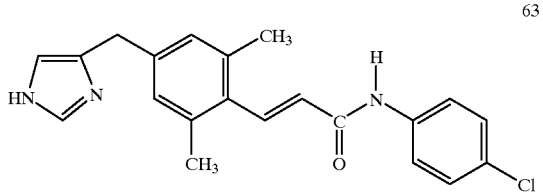

was prepared.

EXAMPLE 66

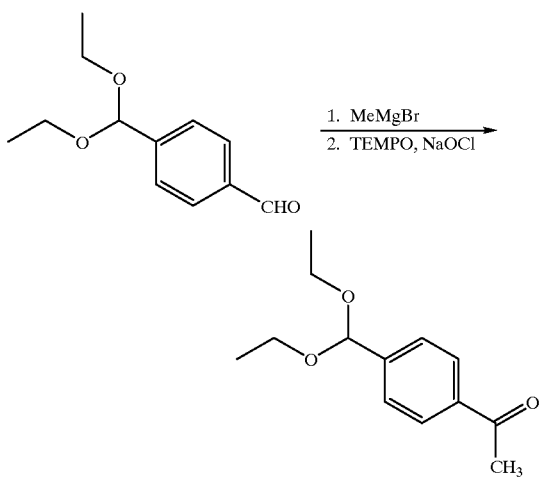

A solution of terephthalaldehyde mono-(diethyl acetal) (5.0 ml, 25 mmol) in THF (100 ml) was treated with 1.4 M MeMgBr (21.5 ml, 30 mmol). After 30 min, the reaction mixture was added to water (200 ml) and extracted with EtOAc (200 ml). The organic layer was washed with brine (100 ml), dried with $Na_2SO_4$ and concentrated to give the crude alcohol intermediate as a colorless oil.

To a 0° C. solution of the crude alcohol intermediate dissolved in EtOAc (150 ml) was added a solution of NaBr (2.60 g, 25.3 mmol) in sat. aq. $NaHCO_3$ (150 ml) and TEMPO (39 mg, 0.25 mmol). While rapidly stirring the reaction mixture, 0.7 M aq. NaOCl (36 ml, 25 mmol) was added over 20 min then sat. $Na_2S_2O_3$ (50 ml). After warming to RT, the reaction mixture was partitioned and the aqueous layer was extracted with EtOAc (3×50 ml). The combined organic layers were washed with brine (100 ml), dried with $Na_2SO_4$ and concentrated to give 4.86 g of the ketone product (21.9 mmol, 87% yield for two steps) as a yellow oil.

Following a procedure similar to that of Example 1, the ketone was converted to the final product. The (E) isomer:

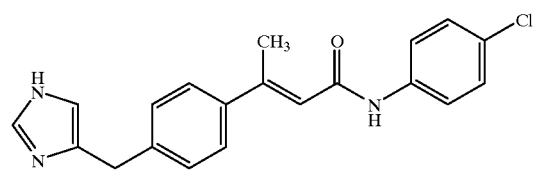

and the (Z) isomer:

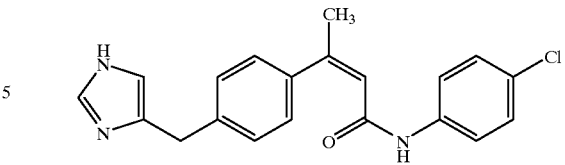

of the final product were obtained.

The data for these two isomers were:

(E)-N-(4-chlorophenyl)-3-[4-[(1H-imidazol-4-yl)methyl]-phenyl]-3-methyl-2-propenamide: $^1$H-NMR $(CD_3OD)\delta$ 2.64 (s, 3H), 4.03 (s, 2H), 6.43 (s, 1H), 6.88 (s, 1H), 7.35 (d, J=8 Hz, 2H), 7.37 (d, J=9 Hz, 2H), 7.57 (d, J=8 Hz, 2H), 7.68 (s, 1H), 7.70 (d, J=9 Hz, 2H); HRMS (M+H$^+$): m/e calc'd $[C_{20}H_{19}N_3OCl]^+$: 352.1217, found 352.1214.

(Z)-N-(4-chlorophenyl)-3-[4-[(1H-imidazol-4-yl)methyl]-phenyl]-3-methyl-2-propenamide: $^1$H-NMR $(CD_3OD)\delta$ 2.27 (s, 3H), 3.99 (s, 2H), 6.16 (s, 1H), 6.83 (s, 1H), 7.4 (m, 6H), 7.43 (d, J=8 Hz, 2H), 7.65 (s, 1H); HRMS (M+H$^+$): m/e calc'd $[C_{20}H_{19}N_3OCl]^+$: 352.1217, found 352.1227.

Mass Spectral Data of Compounds:

| Compound # | Calculated | Found |
|---|---|---|
| 1 | 338.1060 | 338.1066 |
| 2 | 352.1217 | 352.1218 |
| 3 | 366.1373 | 366.1372 |
| 4 | 352.1217 | 352.1214 |
| 5 | 380.1530 | 380.1525 |
| 6 | 304.1540 | 304.1449 |
| 7 | 310.1919 | 310.1917 |
| 8 | 366.1373 | 366.1371 |
| 9 | 380.1530 | 380.1532 |
| 10 | 346.1919 | 346.1924 |
| 11 | 362.1869 | 362.1862 |
| 12 | 371.1872 | 371.1875 |
| 15 | 338.1327 | 338.1331 |
| 16 | 350.1669 | 350.1667 |
| 17 | 333.1715 | 333.1720 |
| 18 | 350.1669 | 350.1670 |
| 19 | 366.1373 | 366.1372 |
| 21 | 308.1399 | 308.1405 |
| 22 | 346.1919 | 346.1916 |
| 23 | 360.2076 | 360.2074 |
| 24 | 358.1919 | 358.1924 |
| 26 | 368.1763 | 368.1763 |
| 28 | 400.0983 | 400.0993 |
| 29 | FAB = 332 (M + 1) | |
| 30 | 372.0670 | 372.0673 |
| 31 | 338.1060 | 338.1069 |
| 32 | 329.1402 | 329.1402 |
| 33 | 334.1556 | 334.1559 |
| 35 | 322.1356 | 322.1356 |
| 36 | 322.1356 | 322.1356 |
| 37 | 388.1273 | 388.1274 |
| 38 | 388.1273 | 388.1270 |
| 39 | 332.1763 | 332.1762 |

Additional mass spectral data are: (1) Compound No. 61-352 (M+1); and (2) Compound No. 62-FAB 337 (M+1).

$H_3$ Receptor Binding Assay

The source of the $H_3$ receptors in this experiment was guinea pig brain. The animals weighed 400–600 g. The brain tissue was homogenized using a Polytron in a solution of 50 mM Tris, pH 7.5. The final concentration of tissue in the homogenization buffer was 10% w/v. The homogenates were centrifuged at 1,000×g for 10 min. in order to remove clumps of tissue and debris. The resulting supernatants were then centrifuged at 50,000×g for 20 min. in order to sediment the membranes, which were next washed three times in homogenization buffer (50,000×g for 20 min. each). The membranes were frozen and stored at −70° C. until needed.

All compounds to be tested were dissolved in DMSO and then diluted into the binding buffer (50 mM Tris, pH 7.5) such that the final concentration was 2 μg/ml with 0.1% DMSO. Membranes were then added (400 μg of protein) to the reaction tubes. The reaction was started by the addition of 3 nM [$^3$H]R-α-methylhistamine (8.8 Ci/mmol) or 3 nM [$^3$H]N$^\alpha$-methylhistamine (80 Ci/mmol) and continued under incubation at 30° C. for 30 min. Bound ligand was separated from unbound ligand by filtration, and the amount of radioactive ligand bound to the membranes was quantitated by liquid scintillation spectrometry. All incubations were performed in duplicate and the standard error was always less than 10%. Compounds that inhibited more than 70% of the specific binding of radioactive ligand to the receptor were serially diluted to determine a $K_i$ (nM).

| Compound # | $K_i$ (nM) |
|---|---|
| 1 | 2 |
| 2 | 23 |
| 3 | 7 |
| 4 | 45 |
| 5 | 35 |
| 6 | 2 |
| 7 | 26 |
| 8 | 11 |
| 9 | 10 |
| 10 | 19 |
| 11 | 7 |
| 12 | 45 |
| 13 | 270 |
| 15 | 12 |
| 16 | 10 |
| 17 | 190 |
| 18 | 10 |
| 19 | 12 |
| 20 | 580 |
| 21 | 110 |
| 22 | 6 |
| 23 | 37 |
| 24 | 220 |
| 25 | 400 |
| 26 | 200 |
| 27 | 1000 |
| 28 | 36 |
| 29 | 17 |
| 30 | 12 |
| 31 | 4 |
| 32 | 4 |
| 33 | 3 |
| 34 | 2 |
| 35 | 1 |
| 36 | 5 |
| 37 | 8 |
| 38 | 10 |

From these test results and the background knowledge about the compounds described in the references in the section "Background of the Invention", it is to be expected that the compounds of the invention would be useful in treating inflammation, allergy, diseases of the GI-tract, cardiovascular disease, or disturbances of the central nervous system.

Pharmaceutically acceptable inert carriers used for preparing pharmaceutical compositions from the compounds of Formula I and their salts can be either solid or liquid. Solid form preparations include powders, tablets, dispersible granules, capsules, cachets and suppositories. The powders and tablets may comprise from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

Liquid form preparations include solutions, suspensions and emulsions, for example water or water-propylene glycol solutions for parenteral injection. Liquid form preparations may also include solutions for intranasal administration.

Also included are solid form preparations which are intended for conversion, shortly before use, into liquid form preparations for either oral or parenteral administration. Such liquid forms include solutions, suspensions and emulsions.

Aerosol preparations suitable for inhalation may include solutions and solids in powder form, which may be in combination with a pharmaceutically acceptable carrier, such as an inert compressed gas.

For preparing suppositories, a low melting wax such as a mixture of fatty acid glycerides or cocoa butter is first melted, and the active ingredient is dispersed homogeneously therein as by stirring. The molten homogeneous mixture is then poured into conveniently sized molds, and allowed to cool and thereby solidify.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose. The quantity of active compound in a unit dose of preparation may be varied or adjusted from about 0.1 mg to 1000 mg, more preferably from about 1 mg to 500 mg, according to the particular application.

The actual dosage employed may be varied depending upon the requirements of the patient and the severity of the condition being treated. The determination of the proper dosage for a particular condition is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day it desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 1 mg to 2000 mg/day, preferably 10 to 1000 mg/day, in one to four divided doses to achieve relief of the symptoms. The compounds are non-toxic when administered at therapeutic doses.

The following are examples of pharmaceutical dosage forms which contain a compound of the invention. As used therein, the term "active compound" is used to designate one of the compounds of the formula I or salt thereof, especially compounds 6 and 29 herein (as free base), namely N-[(4-chlorophenyl)methyl]-4-[(1H-imidazol-4-yl)methyl] benzene methanimidamide and N-[(4-chlorophenyl) methyl]-4-[(1H-imidazol-4-yl)methyl]benzene ethanimidamide, or the dihydrochloride thereof, but any other compound of the formula I or salt thereof can be substituted therefor:

Pharmaceutical Dosage Form Examples

EXAMPLE A

Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|  | Total | 300 | 700 |

Method of Manufacture

Mix Items No. 1 and 2 in a suitable mixer for 10 to 15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1 to 3 minutes. Compress the mixture to appropriate size and weigh on a suitable tablet machine.

EXAMPLE B

Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 4 | 7 |
|  | Total | 250 | 700 |

Method of Manufacture

Mix Items No. 1, 2 and 3 in a suitable blender for 10 to 15 minutes. Add Item No. 4 and mix for 1 to 3 minutes. Fill the mixture into suitable two-piece hard gelatin capsules on a suitable encapsulating machine.

While a number of embodiments of this invention are described herein, it is apparent that the embodiments can be altered to provide other embodiments that utilize the compositions and processes of this invention. Therefore, it will be appreciated that the scope of this invention includes alternative embodiments and variations which are defined in the foregoing Specification and by the claims appended hereto; and the invention is not to be limited to the specific embodiments that have been presented herein by way of example.

What is claimed is:

1. A compound of the formula:

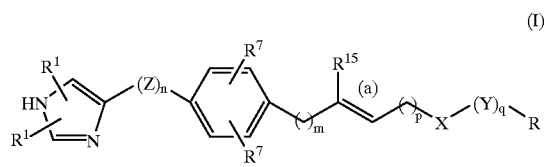

(I)

or a pharmaceutically acceptable salt or solvate thereof, wherein:

the double bond (a) is of the E or Z, configuration;

each $R^1$ is independently selected from the group consisting of hydrogen, lower alkyl, trihalomethyl, phenyl and benzyl;

each $R^7$ is independently selected from the group consisting of hydrogen, lower alkyl, halogen, trihalomethyl, $NR^{10}R^{11}$, or a group $OR^{10}$, whereby $R^{10}$ and $R^{11}$ are independently selected from hydrogen, lower alkyl or trihalomethyl;

X is —$CONR^5$—; —$SO_2$—, —S—; —CO—; —COO—; —$CN(OR^5)NR^5$—; —$C(NR^5)NR^5$—; —$SONR^5$—; —$SO_2NR^5$— and, provided p is not zero, X is also —O—; —$NR^5$—; —$NR^5CONR^5$—; —$OCONR^5$—; —O—CO— or —$NR^5CO$—;

Y is $C_1$–$C_3$-alkyl, unsubstituted or substituted at any carbon atom of the group by one substituent $R^5$;

Z is $C(R^1)_2$; wherein no more than two $R^1$ groups are other than hydrogen;

n is 1 or 2;

m is 0 or 1;

p is 0 or 1;

q is 0 or 1;

R is selected from:
(1) $C_3$ to $C_7$ cycloalkyl,
(2) heterocyclic groups,
(3) aryl,
(4) heteroaryl,
(5) substituted $C_3$ to $C_7$ cycloalkyl having 1–3 substituents independently selected from the group consisting of lower alkyl trihalomethyl and $NR^{10}R^{11}$, wherein $R^{10}$ and $R^{11}$ are independently selected from hydrogen, lower alkyl or trihalomethyl,
(6) substituted heterocyclic having 1–3 substituents independently selected from the group consisting of lower alkyl trihalomethyl and $NR^{10}R^{11}$, wherein $R^{10}$ and $R^{11}$ as defined above, said substituents being bound to carbon atoms in the ring such that the total number of substituents in the ring is 1 to 3; and wherein the heterocyclic ring contains nitrogen atoms, said nitrogen atoms are unsubstituted or substituted with lower alkyl;
(7) substituted aryl having 1–3 substituents independently selected from the group consisting of lower alkyl, halogen, trihalomethyl, CN, $NO_2$, $OR^{10}$ or $NR^{10}R^{11}$, wherein $R^{10}$ and $R^{11}$ as defined above,
(8) substituted heteroaryl having 1–3 substituents independently selected from the group consisting of lower alkyl, halogen, trihalomethyl, CN, $NO_2$, $OR^{10}$ or $NR^{10}R^{11}$, wherein $R^{10}$ and $R^{11}$ are as defined above; and each $R^5$ independently represents hydrogen, lower alkyl or poly-halo-loweralkyl.

2. The compound of claim 1 wherein both R⁷ are hydrogen.

3. The compound of claim 2 wherein n is 1.

4. The compound of claim 3 wherein R¹ is hydrogen and R is selected from: (1) phenyl substituted by one or two substitutents selected from; lower alkyl, halogen, trihalomethyl, CN, NO₂, OR¹⁰ or NR¹⁰R¹¹, wherein R¹⁰ and R¹¹ as defined above, or (2) pyridyl substituted by one or two substitutents selected from: lower alkyl, halogen, trihalomethyl, CN, NO₂, OR¹⁰ or NR¹⁰R¹¹, wherein R¹⁰ and R¹¹ as defined above.

5. The compound of claim 4 wherein R represents phenyl substituted by or pyridyl substituted by one or two substituents selected from: halogen, methoxy, CF₃, CN or OCF₃.

6. The compound of claim 5 wherein said substituent is chlorine or fluorine.

7. The compound of claim 5 wherein R is (1) mono-substituted phenyl wherein said substituent is in the 3- or the 4-position or (2) a di-substituted phenyl wherein the two substituents are the same and are in the 3,5-positions.

8. The compound of claim 7 wherein X is —CONR⁵.

9. The compound of claim 8 wherein m is 0.

10. The compound of claim 9 wherein (1) p is 0 and (2) q is 0 or 1, wherein when q is 1, then Y represents —CHR⁵CHR⁵— wherein one R⁵ is hydrogen.

11. The compound of claim 10 wherein said substituent is chlorine or fluorine.

12. The compound of claim 1 selected from:

(IIA)

(IIB)

(IIIA)

or (IVA)

13. The compound of claim 12 wherein R is (1) mono-substituted phenyl wherein said substituent is in the 3- or the 4-position or (2) a di-substituted phenyl wherein the two substituents are the same and are in the 3,5-positions.

14. The compound of claim 7 having the formula (IIA)

or (IIB)

wherein R is selected from (1) phenyl, (2) 4-Cl-phenyl, (3) 3,5-dimethyl-phenyl, (4) 3-F-phenyl, (5) 4-F-phenyl, (6) 3-methoxy-phenyl or (7) 3-CN-phenyl.

15. The compound of claim 7 having the formula (IIIA)

or (IVA)

wherein m is 0 or 1 and R is selected from (1) phenyl, (2) 4-chlorophenyl, (3) 3,5-dimethylphenyl, (4) 3-fluorophenyl, (5) 4-fluorophenyl, (6) 3-methoxyphenyl or (7) 3-cyanophenyl.

16. The compound of claim 7 wherein X is selected from —NH—, —SO₂—, —O— or —SO₂NH—.

17. The compound of claim 16 wherein the substituent is chlorine or fluorine.

18. The compound of claim 16 wherein R is (1) phenyl, (2) phenyl substituted in the 3- or 4-position by Cl, F, CN or OCH₃, or (3) phenyl substituted in the 3- and 5-positions by Cl, F, CF₃, CH₃, OCH₃ or OCF₃.

19. The compound of claim 18 wherein (1) m is 0 or 1, (2) p is 1 and (3) q is 0 or 1, wherein when q is 1 then Y represents —CH₂CH₂—.

20. A pharmaceutical composition comprising a compound of claim 1, or a pharmaceutically acceptable salt or solvate thereof, in combination with a pharmaceutically acceptable carrier or excipient.

21. A method of treating allergy, inflammation, cardiovascular disease, hypotension, glaucoma, sleeping disorders, diseases of the GI-tract, states of hyper and hypo motility of the gastrointestinal tract, or disturbances of the central nervous system, hypo and hyperactivity of the central nervous system, Alzheimer's, schizophrenia, obesity and migraines, comprising administering an effective amount of a compound of claim 1, or a pharmaceutically acceptable acid addition salt or solvate thereof, to a patient in need of such treatment.

22. A method for treatment of upper airway allergic responses comprising administering to a patient in need of such treatment a compound, or a salt or solvate thereof, of claim 1 in combination or admixture with a histamine $H_1$ receptor antagonist.

23. The method of claim 22 wherein said $H_1$ antagonist is selected from: loratadine, descarboethoxyloratadine, fexofenadine, cetirizine.

24. The method of claim 23 wherein said $H_1$ antagonist is selected from: loratadine or descarboethoxyloratadine.

* * * * *